(12) United States Patent
Klein et al.

(10) Patent No.: US 6,787,129 B1
(45) Date of Patent: Sep. 7, 2004

(54) CASTOR POLYESTER AS GLOSS AGENTS IN ANIONIC SYSTEMS

(75) Inventors: Kenneth Klein, Fair Lan, NJ (US); Irwin Paleksky, Clifton, NJ (US); Anthony J. O'Lenick, Jr., Dacula, GA (US)

(73) Assignee: Zenitech LLC, Old Greenwich, CT (US)

( * ) Notice: Subject to any disclaimer, the term of this patent is extended or adjusted under 35 U.S.C. 154(b) by 76 days.

(21) Appl. No.: 10/340,518

(22) Filed: Jan. 13, 2003

(51) Int. Cl.⁷ ............................ A61K 7/075; C11D 1/12; C11D 3/37

(52) U.S. Cl. .................. 424/70.11; 424/70.1; 424/70.5; 424/70.22; 424/70.24; 424/78.03; 510/119; 510/475; 510/492; 514/546; 514/547; 528/295.5

(58) Field of Search ................................ 424/70.1, 70.5, 424/70.11, 70.22, 70.24, 78.03; 510/119, 475, 492; 514/546, 547; 528/295.5

(56) References Cited

U.S. PATENT DOCUMENTS

| | | |
|---|---|---|
| 4,788,006 A | 11/1988 | Bolich et al. |
| 6,342,527 B1 * | 1/2002 | O'Lenick et al. ............ 514/547 |

* cited by examiner

*Primary Examiner*—Brian P. Mruk

(57) ABSTRACT

The invention relates to a blend, and a process for its use, which is made up of specific castor polyesters and anionic surfactants, which when used to clean the hair provide detergency and cleaning attributes, but surprisingly also provide the hair with gloss.

34 Claims, No Drawings

CASTOR POLYESTER AS GLOSS AGENTS IN ANIONIC SYSTEMS

BACKGROUND OF THE INVENTION

The current invention relates to a composition, and a process for its use, which comprises specific castor polyesters and anionic surfactants, which when used to clean the hair provide detergency and cleaning attributes, but surprisingly also provide the hair with gloss. The castor polyester, which is water insoluble, surprisingly can be added to the anionic surfactant, have no effect upon foam, and provide gloss to the hair when dry. The combination of these properties makes these materials very well suited to personal care applications.

It has long been the desire of personal care formulators to provide several benefits to the consumer as a result of washing the hair. The washing of the hair, first and foremost needs to provide cleansing properties. That is the shampoo needs to have detergency. Oils on the hair, soils from the environment and residuals from other treatment products, like styling gels need to be removed from the hair. Anionic surfactants selected from the group consisting of sulfates, ether sulfates and alpha olefin sulfonates have long been used in cleaning hair. The problem is that if not formulated correctly these compounds can strip the hair and leave it dry, and in a state with high levels of static. These are undesirable conditions.

Much work has been done to address the incorporation of conditioners into the product. These include the so-called two in one products that contain silicone. An example of this are it U.S. Pat. No. 4,788,006 issued November 1988 to Bolich et al. It contains silicone, a cationic quat and an anionic surfactant. These formulations do not recognize the functionality of the castor polymer and its ease of formulation in making a simple effective conditioner.

Another very desirable attribute that is desired on the hair is gloss. Hair that is clean and has a gloss is generally considered more aesthetically appealing. The problem with getting gloss is that it is generally obtained with the use of a water-insoluble oil. The oil is generally applied from a volatile solvent like cyclomethicone or isopropanol. These volatile solvents are not considered appropriate for today's products. Specifically, they are flammable and are not considered green by today's environmentally conscious consumer.

Attempts to include the gloss agent in the shampoo have resulted in failure. Specifically, the oil phase does not formulate into the water phase without emulsifiers. The resulting emulsion is generally white and opaque and significantly does not provide the foam or detergency in the shampoo. The oil interferes with the foam and detergency.

We have surprisingly found that incorporation between 0.1 and 5.0% of a specific castor polyester in anionic surfactants selected from the group consisting of sulfates, ether sulfates and alpha olefin sulfonates, allows for the formulation of detergent systems that provide gloss, foam and good detergency in one product. The castor polyesters useful in the practice of the current invention are outlined in U.S. Pat. No. 6,342,527 issued on Jan. 29, 2002 to O'Lenick and LaVay, assigned to Zenitech LLC, incorporated herein by reference.

OBJECTIVE OF THE INVENTION

The present invention has as its objective a composition that comprises a blend of anionic surfactants selected from the group consisting of sulfates, ether sulfates and alpha olefin sulfonates, and polymeric castor polyesters, which can be used in personal care compositions, like shampoos, to provide foam, detergency and gloss when applied to the hair.

Another objective of the invention is to provide a process for simultaneously cleaning and glossing hair, which comprises contacting the hair with an effective cleaning concentration of a composition which comprises a blend of anionic surfactants selected from the group consisting of sulfates, ether sulfates and alpha olefin sulfonate, and polymeric castor polyesters.

BRIEF SUMMARY OF THE INVENTION

The present invention relates to a composition used to clean and provide gloss to the hair. The invention is directed to a hair composition, which comprises;

(1) anionic surfactants selected from the group consisting of sulfates, ether sulfates and alpha olefin sulfonate and (2) a polymeric castor polyester which conforms to the following structure;

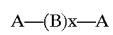

wherein;

A is:

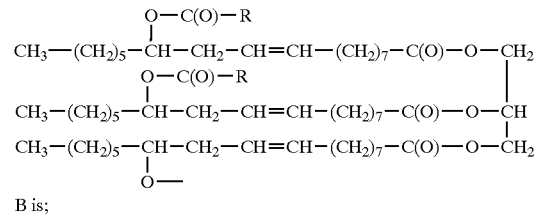

B is;

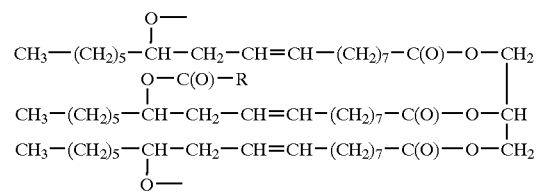

the linking group between all of the O— are succinyl groups conforming to the following structure —C(O)—CH$_2$—CH$_2$—C(O)—;

R is selected from alkyl and alkylene having 5 to 33 carbon atoms;

x is an integer ranging from 1 to 50.

The present invention is directed to a process for simultaneously cleaning and glossing hair, which comprises contacting the hair with an effective cleaning concentration of a composition which comprises a blend of anionic surfactants selected from the group consisting of sulfates, ether sulfates and alpha olefin sulfonate, and polymeric castor polyesters, conforming to the following structure:

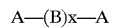

wherein;

A is:

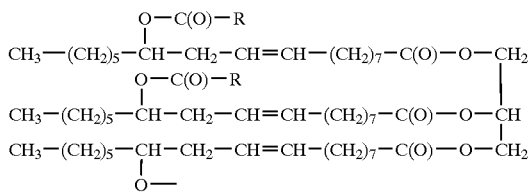

B is;

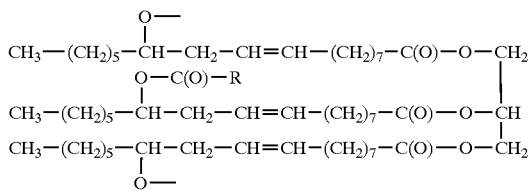

the linking group between all of the O— are succinyl groups conforming to the following structure —C(O)—CH$_2$—CH$_2$—C(O)—;

R is selected from alkyl and alkylene having 5 to 33 carbon atoms;

x is an integer ranging from 1 to 50.

DETAILED DESCRIPTION OF THE INVENTION

Specifically the present invention relates to a composition used to clean and provide gloss to the hair. The invention is directed to a hair composition, which comprises a blend of;

(1) anionic surfactants selected from the group consisting of (a) sulfates conforming to the following structure:

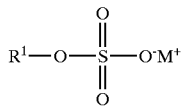

wherein;

R$^1$ is alkyl having from 8 to 18 carbon atoms,

M is selected from the group consisting of Na, K, NH$_4$ (b) ether sulfates, which conform to the following structure:

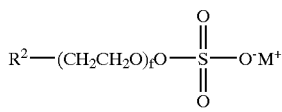

wherein

R$^2$ is alkyl having from 8 to 18 carbon atoms,

M is selected from the group consisting of Na, K, NH$_4$, f is an integer ranging from 1–10.

and (c) alpha olefin sulfonate which conform to the following structure:

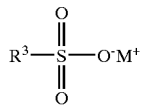

wherein

R$^3$ is alkyl having from 8 to 18 carbon atoms,

M is selected from the group consisting of Na, K, NH$_4$.

and (2) a polymeric castor polyester which conforms to the following structure;

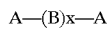

wherein;

A is:

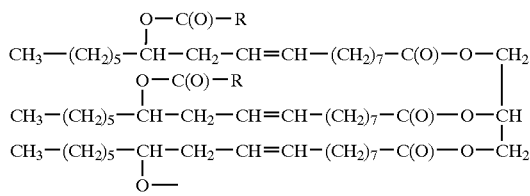

B is;

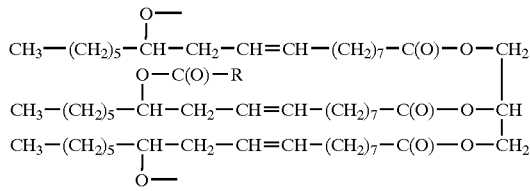

the linking group between all of the O— are succinyl groups conforming to the following structure —C(O)—CH$_2$—CH$_2$—C(O)—;

R is selected from alkyl and alkylene having 5 to 33 carbon atoms;

x is an integer ranging from 1 to 50.

The present invention is specifically directed to a process for simultaneously cleaning and glossing hair, which comprises contacting the hair with an effective cleaning concentration of a composition, which comprises a blend of;

(1) anionic surfactants selected from the group consisting of (a) sulfates conforming to the following structure:

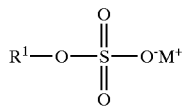

wherein;

R$^1$ is alkyl having from 8 to 18 carbon atoms,

M is selected from the group consisting of Na, K, NH$_4$ (b) ether sulfates, which conform to the following structure:

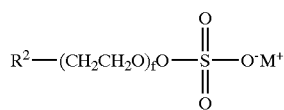

wherein
R² is alkyl having from 8 to 18 carbon atoms,
M is selected from the group consisting of Na, K, NH₄,
f is an integer ranging from 1–10.
and
(c) alpha olefin sulfonate which conform to the following structure:

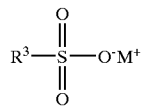

wherein
R³ is alkyl having from 8 to 18 carbon atoms,
M is selected from the group consisting of Na, K, NH₄.
and
(2) polymeric castor polyesters, conforming to the following structure:

A—(B)x—A wherein;

A is:

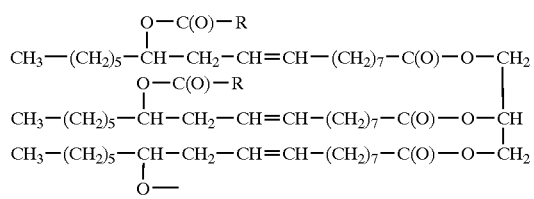

B is;

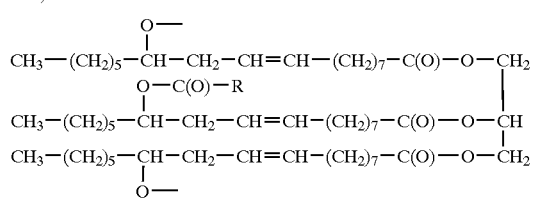

the linking group between all of the O— are succinyl groups conforming to the following structure —C(O)—CH₂—CH₂—C(O)—;
R is selected from alkyl and alkylene having 5 to 33 carbon atoms;
x is an integer ranging from 1 to 50.

PREFERRED EMBODIMENTS

In a preferred embodiment, the ratio of anionic surfactant ranges from 20:1 to 1,000:1.

In another preferred embodiment, the ratio of anionic surfactant ranges from 100:1 to 1,000:1.

In another preferred embodiment, the ratio of anionic surfactant ranges from 100:1 to 500:1.

In a preferred embodiment R¹ is alkyl having 12 carbon atoms.
In a preferred embodiment R¹ is alkyl having 10 carbon atoms.
In a preferred embodiment R¹ is alkyl having 14 carbon atoms.
In a preferred embodiment R² is alkyl having 12 carbon atoms.
In a preferred embodiment R² is alkyl having 10 carbon atoms.
In a preferred embodiment R² is alkyl having 14 carbon atoms.
In a preferred embodiment R³ is alkyl having 12 carbon atoms.
In a preferred embodiment R³ is alkyl having 10 carbon atoms.
In a preferred embodiment R³ is alkyl having 14 carbon atoms.
In a preferred embodiment f is 1.
In a preferred embodiment f is 2.
In a preferred embodiment f is 3.
In a preferred embodiment f is 4.

EXAMPLES

Anionic Surfactants

This group of compounds are detergents and are commercially available from a variety of sources, including Colonial Chemical in South Pittsburg Tenn.

Sulfates

Sulfates are a group of well-known, commercially available compounds that conform to the following structure:

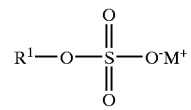

wherein;
R¹ is alkyl having from 8 to 18 carbon atoms,
M is selected from the group consisting of Na, K, NH₄.

[039]
| Example | R¹ | M |
| --- | --- | --- |
| 1 | C8 | Na |
| 2 | C10 | K |
| 3 | C12 | NH₄ |
| 4 | C14 | Na |
| 5 | C16 | Na |
| 6 | C18 | K |

Ether Sulfates

Ether sulfates are a group of well-known, commercially available compounds that conform to the following structure:

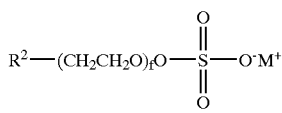

wherein $R^2$ is alkyl having from 8 to 18 carbon atoms,

M is selected from the group consisting of Na, K, $NH_4$.

f is an integer ranging from 1–10.

[042]

| Example | $R^1$ | M | f |
|---|---|---|---|
| 7 | C8 | Na | 1 |
| 8 | C10 | $NH_4$ | 2 |
| 9 | C12 | $NH_4$ | 3 |
| 10 | C14 | Na | 4 |
| 11 | C16 | Na | 5 |
| 12 | C18 | K | 10 |

Alpha Olefin Sulfonate

Alpha olefin sulfonates are a group of well-known, commercially available compounds that conform to the following structure.

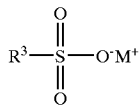

wherein $R^3$ is alkyl having from 8 to 18 carbon atoms,

M is selected from the group consisting of Na, K, $NH_4$.

[045]

| Example | $R^3$ | M |
|---|---|---|
| 13 | C8 | Na |
| 14 | C10 | K |
| 15 | C12 | $NH_4$ |
| 16 | C14 | Na |
| 17 | C16 | Na |
| 18 | C18 | K |

Polymeric Castor Polyester

Polymeric castor polyesters are commercially available from Zenitech LLC, Old Greenwich Conn. They are marketed under the name Zenigloss$^R$. The polymers are 100% active as sold.

[048]

| Example | R | x |
|---|---|---|
| 19 | 6 | 50 |
| 20 | 10 | 10 |
| 21 | 18 | 5 |
| 22 | 26 | 5 |
| 23 | 33 | 2 |

Compositions of the Invention

| | Anionic Surfactant | | Polymeric Castor Polyester | |
|---|---|---|---|---|
| Example | Example | Grams | Example | Grams |
| 24 | 1 | 100.0 | 19 | 0.5 |
| 25 | 2 | 100.0 | 20 | 0.5 |
| 26 | 3 | 100.0 | 21 | 1.0 |
| 27 | 4 | 100.0 | 22 | 1.0 |
| 28 | 5 | 100.0 | 23 | 1.5 |
| 29 | 6 | 100.0 | 19 | 2.0 |
| 30 | 7 | 100.0 | 20 | 2.2 |
| 31 | 8 | 100.0 | 21 | 0.5 |
| 32 | 9 | 100.0 | 22 | 1.9 |
| 33 | 10 | 100.0 | 23 | 5.0 |
| 34 | 11 | 100.0 | 19 | 4.9 |
| 35 | 12 | 100.0 | 20 | 1.3 |
| 36 | 13 | 100.0 | 21 | 0.5 |
| 37 | 14 | 100.0 | 22 | 1.0 |
| 38 | 15 | 100.0 | 23 | 1.0 |
| 39 | 16 | 100.0 | 19 | 5.0 |
| 40 | 17 | 100.0 | 20 | 5.0 |
| 41 | 18 | 100.0 | 21 | 4.8 |

Applications Examples

The products made in examples 24–41 have outstanding detergency and foam when applied to hair and have outstanding conditioning properties including wet comb.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

What is claimed is:

1. A composition used to clean and provide gloss to the hair, which comprises a blend of;

(1) anionic surfactants selected from the group consisting of (a) sulfates conforming to the following structure:

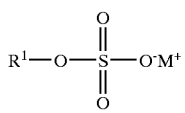

wherein;

$R^1$ is alkyl having from 8 to 18 carbon atoms,

M is selected from the group consisting of Na, K, $NH_4$ (b) ether sulfates, which conform to the following structure:

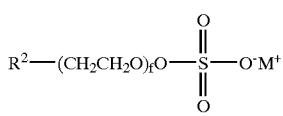

wherein $R^2$ is alkyl having from 8 to 18 carbon atoms,

M is selected from the group consisting of Na, K, $NH_4$, f is an integer ranging from 1–10, and (c) alpha olefin sulfonate which conform to the following structure:

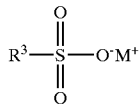

wherein

R$^3$ is alkyl having from 8 to 18 carbon atoms,

M is selected from the group consisting of Na, K, NH$_4$, and (2) a polymeric castor polyester which conforms to the following structure;

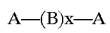

wherein;

A is:

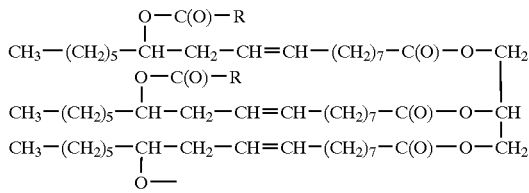

B is;

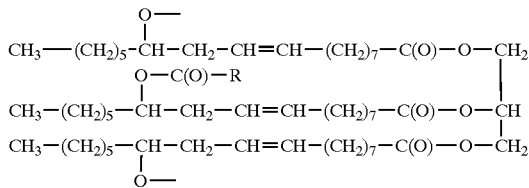

the linking group between all of the O— are succinyl groups conforming to the following structure —C(O)—CH$_2$—CH$_2$—C(O)—;

R is selected from alkyl and alkylene having 5 to 33 carbon atoms;

x is an integer ranging from 1 to 50.

2. A composition of claim 1 wherein the ratio of anionic surfactant ranges from 20:1 to 1,000:1.

3. A composition of claim 1 wherein the ratio of anionic surfactant ranges from 100:1 to 1,000:1.

4. A composition of claim 1 wherein the ratio of anionic surfactant ranges from 100:1 to 500:1.

5. A composition of claim 1 wherein R$^1$ is alkyl having 12 carbon atoms.

6. A composition of claim 1 wherein R$^1$ is alkyl having 10 carbon atoms.

7. A composition of claim 1 wherein R$^1$ is alkyl having 14 carbon atoms.

8. A composition of claim 1 wherein R$^2$ is alkyl having 12 carbon atoms.

9. A composition of claim 1 wherein R$^2$ is alkyl having 10 carbon atoms.

10. A composition of claim 1 wherein R$^2$ is alkyl having 14 carbon atoms.

11. A composition of claim 1 wherein R$^3$ is alkyl having 12 carbon atoms.

12. A composition of claim 1 wherein R$^3$ is alkyl having 10 carbon atoms.

13. A composition of claim 1 wherein R$^3$ is alkyl having 14 carbon atoms.

14. A composition of claim 1 wherein f is 1.

15. A composition of claim 1 wherein f is 2.

16. A composition of claim 1 wherein f is 3.

17. A composition of claim 1 wherein f is 4.

18. A process for simultaneously cleaning and glossing hair, which comprises contacting the hair with an effective cleaning concentration of a composition which comprises a blend of;

(1) anionic surfactants selected from the group consisting of (a) sulfates conforming to the following structure:

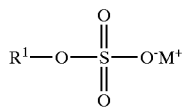

wherein;

R$^1$ is alkyl having from 8 to 18 carbon atoms,

M is selected from the group consisting of Na, K, NH$_4$ (b) ether sulfates, which conform to the following structure:

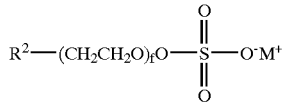

wherein

R$^2$ is alkyl having from 8 to 18 carbon atoms,

M is selected from the group consisting of Na, K, NH$_4$, f is an integer ranging from 1–10, and (c) alpha olefin sulfonate which conform to the following structure:

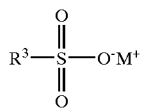

wherein

R$^3$ is alkyl having from 8 to 18 carbon atoms,

M is selected from the group consisting of Na, K, NH$_4$, and (2) polymeric castor polyesters, conforming to the following structure:

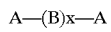

wherein;

A is:

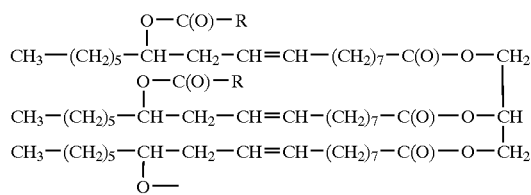

B is;

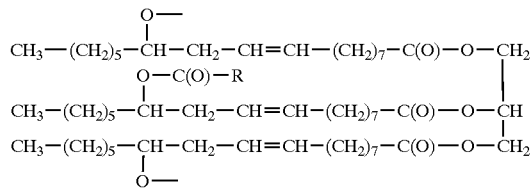

the linking group between all of the O— are succinyl groups conforming to the following structure —C(O)—CH$_2$—CH$_2$—C(O)—;

R is selected from alkyl and alkylene having 5 to 33 carbon atoms;

x is an integer ranging from 1 to 50.

19. A process of claim 18 wherein the ratio of anionic surfactant ranges from 20:1 to 1,000:1.

20. A process of claim 18 wherein the ratio of anionic surfactant ranges from 100:1 to 1,000:1.

21. A process of claim 18 wherein the ratio of anionic surfactant ranges from 100:1 to 500:1.

22. A process of claim 18 wherein $R^1$ is alkyl having 12 carbon atoms.

23. A process of claim 18 wherein $R^1$ is alkyl having 10 carbon atoms.

24. A process of claim 18 wherein $R^1$ is alkyl having 14 carbon atoms.

25. A process of claim 18 wherein $R^2$ is alkyl having 12 carbon atoms.

26. A process of claim 18 wherein $R^2$ is alkyl having 10 carbon atoms.

27. A process of claim 18 wherein $R^2$ is alkyl having 14 carbon atoms.

28. A process of claim 18 wherein $R^3$ is alkyl having 12 carbon atoms.

29. A process of claim 18 wherein $R^3$ is alkyl having 10 carbon atoms.

30. A process of claim 18 wherein $R^3$ is alkyl having 14 carbon atoms.

31. A process of claim 18 wherein f is 1.
32. A process of claim 18 wherein f is 2.
33. A process of claim 18 wherein f is 3.
34. A process of claim 18 wherein f is 4.

* * * * *